US00PP32844P3

(12) United States Plant Patent
Hansen

(10) Patent No.: US PP32,844 P3
(45) Date of Patent: Feb. 23, 2021

(54) ***CAMPANULA* PLANT NAMED 'VIOLET TEACUPS'**

(50) Latin Name: *Campanula carpatica*
Varietal Denomination: Violet Teacups

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 131 days.

(21) Appl. No.: 16/350,795

(22) Filed: Jan. 14, 2019

(65) Prior Publication Data

US 2020/0229337 P1 Jul. 16, 2020

(51) Int. Cl.
*A01H 5/02* (2018.01)
*A01H 6/26* (2018.01)

(52) U.S. Cl.
USPC ..... Plt./414
CPC ..... *A01H 6/264* (2018.05); *A01H 5/02* (2013.01)

(58) Field of Classification Search
USPC ..... Plt./414
CPC ..... A01H 6/264
See application file for complete search history.

*Primary Examiner* — Anne Marie Grunberg

(57) ABSTRACT

The new and distinct bellflower plant, *Campanula* plant named 'Violet Teacups' with dense, compact, mounded habit; cordate to deltoid-medium-green foliage and numerous strong purple campanulate flowers over about a 14 week period beginning in late spring. The new plant is suitable for landscaping as, a specimen, en masse, or in containers.

1 Drawing Sheet

Botanical designation: *Campanula carpatica.*
Cultivar denomination: 'Violet Teacups'.

STATEMENT REGARDING PRIOR DISCLOSURES UNDER 37 CFR 1.77(B)(6)

The first public disclosure of the claimed plant was made by Walters Gardens, Inc. on Feb. 1, 2018 when the claimed plant was displayed as a photograph with short description on a website owned and operated by Walters Gardens, Inc., and the initial sales of the new plants was on Oct. 8, 2018, also by Walters Gardens, Inc., who obtained the plant and all information relating thereto, from the inventor. No plants of *Campanula* 'Violet Teacups' have been sold, in this country or anywhere in the world, nor has any disclosure of the new plant been made, more than one year prior the filing date of this application, and such disclosure within one year was either derived directly or indirectly from the inventor.

BACKGROUND OF THE PLANT

The present invention relates to the new and distinct clustered bellflower herein also referred to as *Campanula* 'Violet Teacups', by the cultivar name, 'Violet Teacups', or as the new plant. The new plant was derived from a cross made on May 14, 2015 from a plant in a greenhouse research facility in Zeeland, Mich. The female parent was a selected seedling privately identified as 'AF-001' (not patented) and the male parent was the same seedling privately identified as 'AF-001'. 'AF-001' is a selection from 'Arend's Form' (not patented) that was self-pollinated. The single selected seedling from this cross represented by 'Violet Teacups' was selected from a group of seedlings by the inventor, isolated and compared in subsequent years to other *Campanula* and subsequently found to be different from all cultivars known to the discoverer and eventually given the breeder code 15-5-1.

Asexual propagation at the same nursery in Zeeland, Mich., USA by basal cuttings has shown 'Violet Teacups' to be stable and reproduce true to type in successive generations since late June 2016.

SUMMARY OF THE PLANT

*Campanula* 'Violet Teacups' has not been observed in all possible environmental conditions. The phenotype may, vary slightly with changes in environments such as light intensity, fertility, water availability, etc. without, however any variation in genotype.

*Campanula* 'Violet Teacups' is distinct from all cultivars known to the inventor in the following traits:

1. Small, cordate to deltoid, serrate, medium-green foliage with compact height and dense mounded habit.
2. Heavily-branched with strong purple bell-shaped flowers clustered at the nodes and ends of stems.
3. Long flowering period beginning in late spring and continuing for at about 14 weeks.

Plants of *Campanula* 'Violet Teacups' are most similar to plants of the seed variety 'Rapido Blue' (not patented). 'Rapido Blue' has a shorter flowering season, less flower coverage in peak flower and the flowers are larger and not as violet in color. 'AF-001' has a flatter flower with shallower cupping. The new plant has denser habit than both 'Arend's Form' and 'AF-001'.

BRIEF DESCRIPTION OF THE DRAWINGS

The color drawings illustrate the overall characteristics of *Campanula* 'Violet Teacups' as a three-year-old plant. The colors are as true as reasonably possible given the technology available. The color values may vary slightly depending on light intensity and quality.

DETAILED BOTANICAL DESCRIPTION

Figure 1:
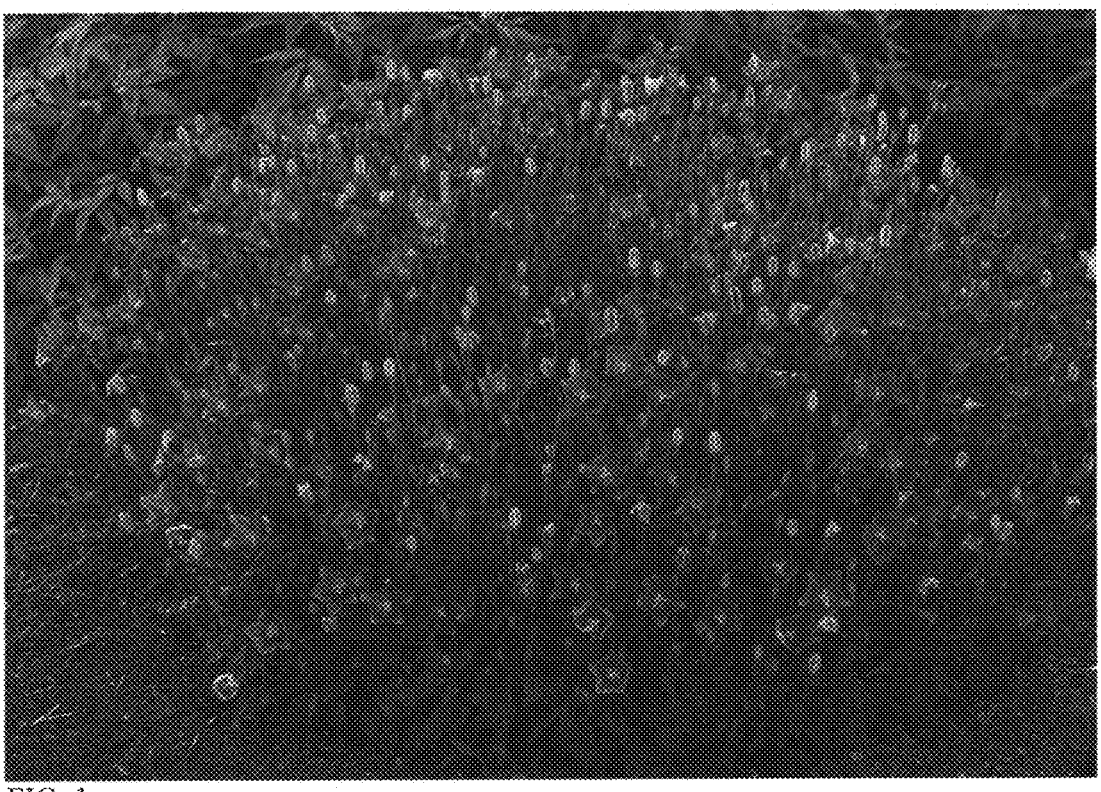
FIG. 1 shows the new plant in a landscape environment.
Figure 2:
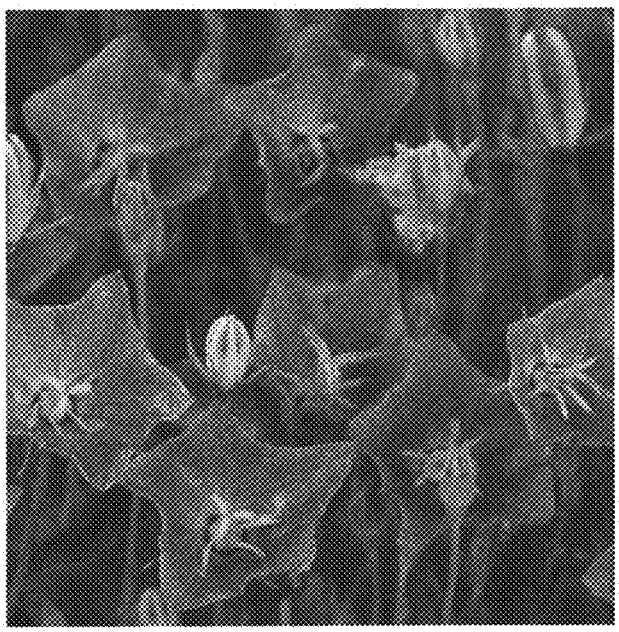
FIG. 2 shows a close-up of the flowers and buds of the new plant.

The following description is based on one and three-year-old plants growing in a full-sun trial garden and a partially shaded greenhouse in Zeeland, Mich., USA. Environmental conditions for the growing season daytime temperatures range between 12° C. to 35° C., and night temperatures range between 6° C. to 24° C. Except for ordinary dictionary color usage, color references are according to The Royal Horticultural Society Colour Chart, 2015 edition. The new plant has not been observed in all possible growing conditions and may vary in phenotypic characteristics based on water availability, light conditions, fertilizer, temperatures, etc. without varying in genotypic characteristics.

Parentage: Female or seed parent is the seedling selection known only privately as 'AF-001'; male or pollen parent is the same seedling selection known only privately as 'AF-001';

Asexual propagation: Cuttings, about 12 to 20 days to initiate roots; time to finish in a one-gallon container about 12 weeks from an established 25 mm plug;

Plant habit: Rounded mound, herbaceous, perennial, winter-hardy; with heavily-branched flower stems up to 45.0 cm wide and 30.0 cm tall; average about 42.0 cm across and about 28.0 cm tall; with about 10 well-branched stems per plant;

Roots: Finely branched; color nearest RHS NN155B;

Stems: Flexible; glabrous; thin; cylindrical with slight longitudinal ridges; to about 24.0 cm long and 3.0 mm diameter at base;

Stem color: Young stems nearest RHS 183B, mature stems nearest RHS 146D toward base and nearest RHS 146B distally;

Leaves: Cauline alternate; simple; cordate to deltoid; acute apex; truncate to cordate base; margin serrate teeth curved toward apex; adaxial and abaxial surfaces glabrous, matte; up to 45.0 mm long and 33.0 mm wide, average about 30.0 mm long and 21.0 mm wide;

Leaf color: Young expanding leaves adaxial nearest RHS 146A with slight bronze blush of nearest RHS 175D and abaxial nearest RHS 146A with slight bronze blush of nearest RHS 175D; mature leaves adaxial nearest RHS 137A, abaxial between RHS 137C and RHS 137B;

Petiole: Thin; concavo-convex; glabrous both adaxial and abaxial; margin entire; to about 64.0 mm long and 2.5 mm wide at base;

Petiole color: Emerging leaves nearest blend of RHS 176B and RHS 146C adaxial and abaxial, mature leaves adaxial and abaxial nearest RHS 137B along margins and nearest RHS 138B in center;

Veins: Palmate; puberulent, glabrate;

Vein color: Adaxial midrib and secondary veins nearest RHS 191B, abaxial midrib and secondary veins nearest RHS 137B;

Flower: Single; perfect; campanulate; on terminal branches; to about 30.0 mm across, about 18.0 mm tall; attitude outright to upright;

Inflorescence fragrance: Not detected;

Calyx: Protruding; to about 20.0 mm wide and extending about level with corolla base;

Sepals: Typically five; lanceolate; narrowly acute apex to apiculate; truncate base; margin micro-serrulate; glabrous adaxial and abaxial; about 10.0 mm long and about 2.0 mm wide at base;

Sepal color: Abaxial and adaxial nearest RHS 137B;

Flowering period: Beginning late spring, for about 14 weeks; producing about 120 flowers and 100 buds per plant at one time during peak flowering;

Flower longevity: About 5 to 7 days;

Flower buds: One day prior to opening—oblong; longitudinally channeled; rounded apex; about 18.0 mm long and 11.0 mm diameter; four days prior to opening—about 14.0 mm long and 6.0 mm diameter near apex;

Flower bud color: One day prior to opening—nearest RHS 83C; four days prior to opening—nearest RHS N77A;

Peduncle: About 10 per plant; highly branched; cylindrical; glabrous; upright to outright attitude; flexible; about 10 mm diameter at base and 40.0 cm long; about 15 nodes, average internode spacing about 2.1 cm; branches to about 27.5 cm long and 2.0 mm diameter at base;

Peduncle color: Nearest 138B;

Pedicel: Cylindrical; glabrous; thin, flexible; average about 8.5 cm long and 0.5 mm diameter;

Pedicel color: Nearest RHS 138A;

Petals: Typically five; acute apex; basal 13.0 mm fused; glabrous adaxial and abaxial; about 18.0 mm long and 12.0 mm wide above fusion;

Petal color: Adaxial nearest RHS N87A with center nearest RHS N87A; abaxial nearest RHS N87C with three midrib nearest RHS N87D;

Androecium: Typically five;

*Filament*.—About 4.0 mm long and 1.5 mm wide at base and 0.1 mm thick, puberulent, flattened and adpressed along ovary in distal one-half; glabrous distally; color nearest RHS 157C.

*Anther*.—Lanceolate; basifixed; about 4.0 mm long and 15 mm across; color nearest RHS 145C.

*Pollen*.—Not abundant; color between RHS 163C and RHS 163D.

Gynoecium: Syncarpous; half-inferior; about 18.0 mm long;

*Style*.—Cylindrical; puberulent distally, glabrous distally; about 10.0 mm long and 0.5 mm diameter; color nearest RHS 145C.

*Stigma*.—Typically trifid; cochleate distally with maturity; about 6.0 mm long before curling, 3.0 mm long when curled, and 0.5 mm diameter; color nearest RHS 197A when young and nearest RHS 196C when mature.

Fruit: Oblong poricidal capsule; longitudinally carinate; 9.0 mm tall and 5.0 mm wide;

Fruit color: Nearest RHS N200A;

Seed: Flattened ellipsoidal; rounded apex and base; about 1.0 mm long and 0.5 mm across center;

Seed color: Variable, some seeds between RHS 200A and RHS N200A;

*Campanula* 'Violet Teacups' is tolerant of winter temperatures from USDA hardiness at least to zones 4 to 8. The new plant grows best in full-sun with good drainage and adequate moisture. It is not known to be tolerant of diseases and pest that are common to other *Campanula* cultivars.

I claim:

1. The new and distinct cultivar of *Campanula* plant named 'Violet Teacups' as described and illustrated.

* * * * *